United States Patent [19]

Fuson

[11] 4,293,962
[45] Oct. 13, 1981

[54] BONE PLUG INSERTING SYSTEM

[75] Inventor: Robert L. Fuson, Warsaw, Ind.

[73] Assignee: Zimmer USA, Inc., Warsaw, Ind.

[21] Appl. No.: 121,560

[22] Filed: Feb. 14, 1980

[51] Int. Cl.³ ............................ A61F 1/00; A61F 1/24
[52] U.S. Cl. ...................................... 3/1.9; 128/92 C
[58] Field of Search ........................ 3/1.9, 1.91, 1.911, 3/1.912, 1.913; 128/92 C, 92 CA

[56] References Cited

U.S. PATENT DOCUMENTS 4,123,806 11/1978 Amstutz et al. ...................... 3/1.912
4,245,359 1/1981 Stuhmer ......................... 128/92 C X

FOREIGN PATENT DOCUMENTS 6408 1/1980 European Pat. Off. ................. 3/1.9
2017503 10/1979 United Kingdom .................... 3/1.9

OTHER PUBLICATIONS

Zimmer Bone Plug Cutter, Surgical Technique, C. 1979, Zimmer USA, Inc., 5 pp.
Intramedullary Cement Plug to Improve Fixation of the Femoral Head Prosthesis, *The Journal of Bone and Joint Surgery*, Nov. 1977, vol. 59-B, No. 4, p. 512.
Polymethylenethacrylate in the Knee, *The Journal of Bone and Joint Surgery*, Jun. 1976, vol. 58-A, No. 4, pp. 556-557.
DePuy Lidge Bone Plug Inserter-A De Puy advertisement-not dated (believed to be a 1978 date). 1 p.

*Primary Examiner*—Clifford D. Crowder
*Attorney, Agent, or Firm*—Margaret L. Geringer; Richard H. Brink

[57] ABSTRACT

A device for plugging the medullary canal in joint replacement surgery which prevents the cement used for fixation from extending beyond that point where it is useful and which also creates a closed space to facilitate more complete cement filling of the femoral canal or other boney cavities is disclosed. The device is comprised of a tapered cylindrical plug which is threadedly engaged to a long flexible shaft capable of being inserted into the medullary canal. The shaft is disengaged from the plug after the plug is lodged at the appropriate place in the canal. The plug is made of a bio-compatible material.

9 Claims, 5 Drawing Figures

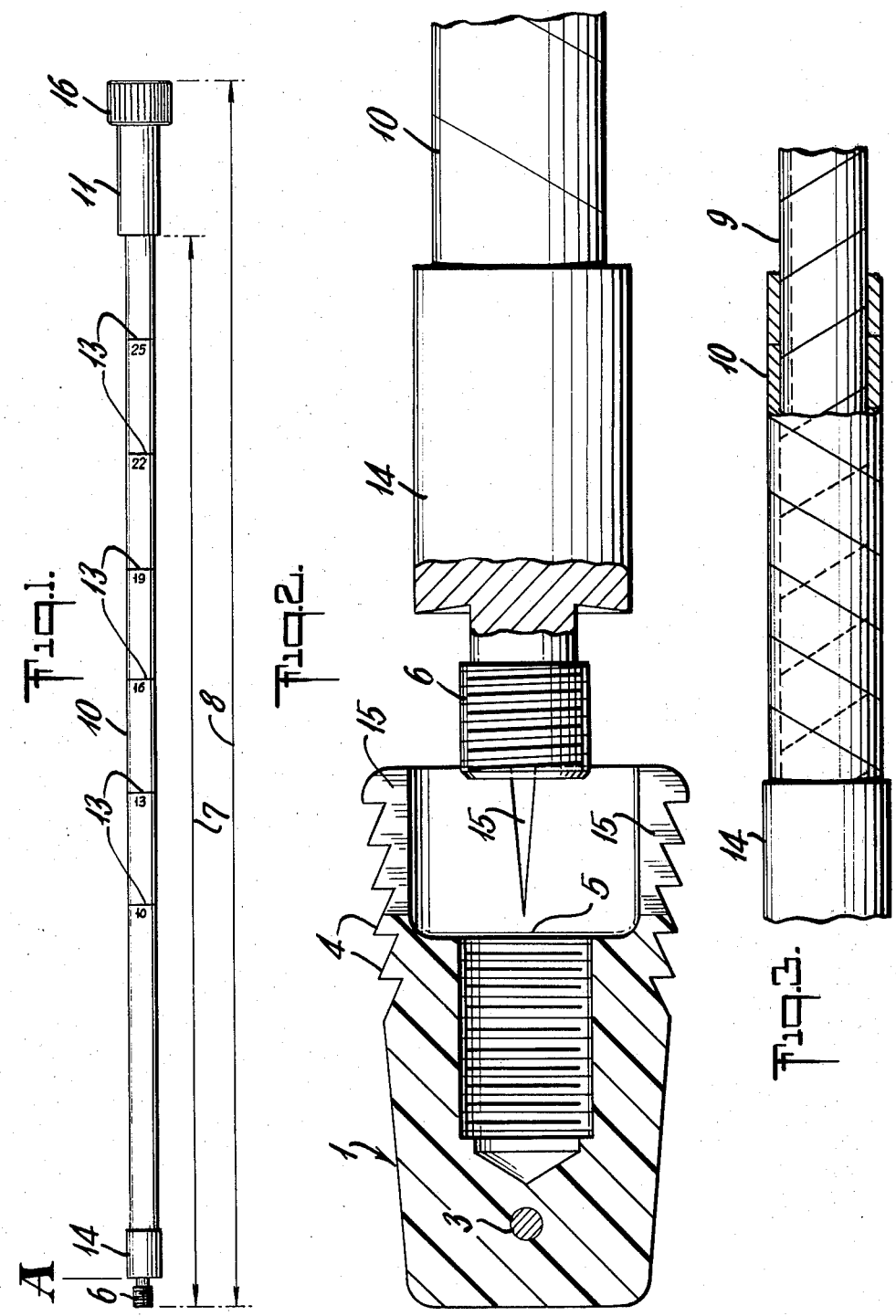

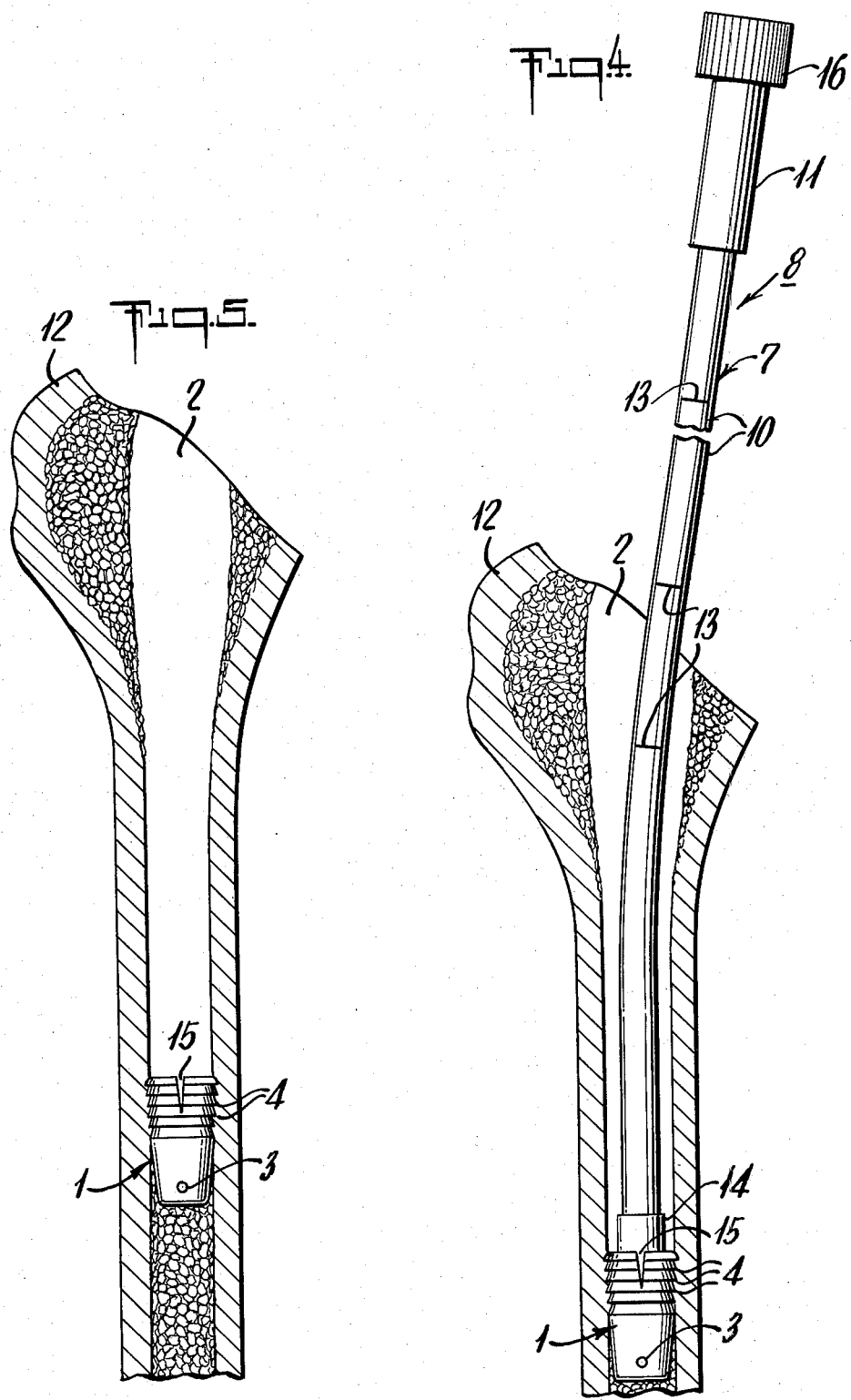

BONE PLUG INSERTING SYSTEM

BACKGROUND OF THE INVENTION

Plugging of the femoral canal has been advocated in the last few years in total hip arthoplasty. A complication of total hip arthroplasty has commonly been the loosening of the femoral component. A factor which contributes to this is the failure between the bone/cement interface. It has been shown that some type of plugging of the canal prevents the extension of the bone cement beyond the point where it is useful and it also creates a closed space which facilitates more complete filling of the femoral canal. Once the canal is plugged, the canal is filled completely and efficiently with acrylic cement (bone cement). Then the stem of the prosthesis is inserted into the cement filled canal. Due to the closed space, there is a rise in pressure in the acrylic cement during stem insertion, which enhances a stronger cement/stem interface and also enhances a stronger cement/bone interface because the higher pressure forces cement to penetrate the interstices of the bone.

A variety of techniques have been advocated in blocking off the femoral canal, including a bolus of doughy cement, a plug cut from bone which has usually been resected from the femoral head or neck at the time of surgery, an inflated balloon, and a plastic plug. In any case, the material must be a bio-compatible material.

OBJECTS OF THE INVENTION

A principal object of the invention is to provide a bio-compatible plugging device and a means for inserting said plugging device into the medullary canal in a simple but positive fashion which would assure good blockage of the canal.

Another object of the invention is to provide such a device which requires only a minimum of relatively simple and convenient to use parts.

A further object is to provide a device in which the inserter can easily be disengaged from the plug when the plug is positioned in the appropriate position in the canal.

A still further object of this invention is to provide an inserter which can easily and conveniently be used with a selected number of different size bone plugs so that plugs of appropriate size can be provided for the different sizes of medullary canals of various long bones such as the femur, the tibia, the humerus and the ulna.

A still further object of this invention is to provide a simple means of measuring the depth at which the plug is placed in the medullary canal.

A further object of this invention is to provide a plugging means which is radiopaque for post operative x-ray evaluation of the plug.

SUMMARY OF THE INVENTION

The plug inserting system includes a means for plugging the medullary canal by use of a tapered plug, made of a bio-compatible material, which is used to block off the canal distal to the tip of the prosthesis stem. The device also includes an inserter which is comprised of a long flexible shaft with a handle on the proximal end of the shaft and a small threaded tip on the distal end of the shaft which is used to engage a threaded hole in the proximal portion of the plug. There are a variety of sizes of plugs provided to fit different diameters of medullary canals. The appropriate size plug is inserted to a calculated depth which is easily measured by the incremental depth markings on the shaft of the inserter. Pressure is exerted to create a tight fit between the plug and the canal. The inserter is then unthreaded from the plug and removed, and the rest of the surgical procedure is carried out.

DRAWINGS

In order that the manner in which the foregoing and other objects are achieved can be understood in detail, one particularly advantageous embodiment of the invention will be described with reference to the accompanying drawings, which form part of the original disclosure of this application, and wherein:

FIG. 1 is a side elevational view of the inserting means.

FIG. 2 is an enlarged fragmentary side elevational view partially in cross-section illustrating the threaded tip of the inserting means entering the threaded hole of the plugging means.

FIG. 3 is an enlarged fragmentary side elevational view partially in cross-section illustrating the inner and outer spiral windings of the flexible shaft.

FIG. 4 is a view partially in longitudinal cross-section and partially in side elevation, showing the bone plug inserter inserting the bone plug into the femoral medullary canal.

FIG. 5 is a view partially in longitudinal cross-section and partially in side elevation, showing the plug lodged in position in the femoral canal after the inserter has been removed from the plug.

DETAILED DESCRIPTION OF THE INVENTION

FIG. 4 illustrates the plug inserting device according to the invention. The device is comprised of a means for plugging the medullary canal by use of a tapered plug 1 and an inserter 8. The inserter 8 is comprised of a long flexible shaft 7 with a handle 11, preferably cylindrical, on the proximal end of the shaft 7. A small threaded tip 6 is located on the distal end of the shaft 7, as shown in FIG. 1, and it is used to engage a threaded hole 5 in the proximal portion of the plug 1, as shown in FIG. 2.

The bone plugs 1 come in a variety of diameters in order to accommodate varying diameters of femoral canals 2. The plug 1 is made of a bio-compatible material. In the preferred embodiment of this invention, the material used is ultra-high molecular weight polyethylene (UHMWPE). A small diameter X-ray wire 3 is embedded in the UHMWPE plug, as shown in FIGS. 2, 4 and 5, so that the plug 1 can be located after insertion for post operative X-ray evaluation of the plug. An alternate method of making the plug 1 radiopaque is to mix barium sulfate in the UHMWPE which would also make the plug 1 visible on post operative X-rays.

As shown in FIGS. 2, 4 and 5, the plug 1 is tapered with the larger diameter at the proximal end of the plug 1 and the diameter decreasing gradually to the distal end of the plug 1. The proximal portion contains a series of tooth-like steps 4 in which the diameter of the plug decreases perpendicular to the length of the plug and then tapers back out toward the distal end and approaching the original diameter, but with the outer diameter of each successive step being slightly less in diameter than the previous step as the steps progress from the proximal end toward the distal end of the plug. Each step 4 is a continuous ring about the plug 1, as illustrated in FIGS. 4 and 5. The taper of the plug 1 along with the tapering steps 4 allow for secure wedging of the plug 1 in the canal 2. The tapered design also facilitates insertion of plug 1 into the canal 2. Longitudinal notches 15 are located on the proximal portion of plug, as shown. The notches 15 which are preferably V-shaped, contract as the plug 1 is inserted and expand after inserter 8 is removed, to help provide more secure positioning in the medullary canal.

The proximal end of the plug 1 contains a threaded hole 5, as shown in FIG. 2, which is to engage with the threaded distal tip 6 of the shaft 7 of the inserter 8. The shaft 7 of the preferred embodiment of this invention is flexible to follow the contours of the medullary canal. It consists of an inner spiral metal winding 9 and an outer spiral winding 10, as shown in FIG. 3. The inner spiral 9 is wound in the clockwise direction and the outer spiral 10 is wound in the counterclockwise direction. The design of the spiral windings 9 and 10 gives the shaft 7 its flexibility. This type flexible shaft has been used in the past on other instruments requiring a flexible shaft. A rigid shaft could also be used to insert the plug. A handle 11 is attached to the flexible winding on the proximal end of the shaft. The cylindrical handle has a smaller diameter where it attaches to the flexible portion of the shaft and then steps to a larger knurled diameter 16 at the proximal end of the handle 11.

MODE OF OPERATION OF THE INVENTION

FIG. 4 illustrates a plug 1 and inserting device 8 according to the invention in place in the femoral medullary canal 2 of a femur 12. Before insertion, the patient is anesthetized and prepped for total hip arthroplasty. The head and neck of the femur are resected in the conventional manner. The femoral canal 2 is prepared and cleaned out by means of a rasp and reamers. Care must be taken to remove only loose and soft tissue. The medullary canal diameter must be estimated at the depth at which the plug 1 is to be placed, so that the appropriate diameter plug can be chosen. The plus 1 should be placed at a depth such that the plug 1 will be lodged about one inch distal to the distal tip of the stem of the hip prosthesis. The diameter of the canal is estimated at the desired depth by preoperative X-rays or physical measurement.

The appropriate size of the plug is chosen so that its diameter is slightly larger than the diameter of the canal at the depth the plug is to be positioned.

The plug is threaded onto the threaded tip 6 of the inserter 8. The plug 1 is then inserted down into the canal 2 to the appropriate depth. The depth of insertion is controlled by the incremental measurements 13 marked on the shaft. The incremental measurements are located from point A on the distal end of cylindrical end portion 14 of the shaft 7 as shown in FIG. 1. The handle 11 of the inserter can be tapped lightly with a mallet to lodge the tapering steps 4 of the plug into the inner wall of the medullary canal to secure a tight fit.

The inserter 8 is then unthreaded from the plug 1 and removed from the femoral canal 2 as shown in FIG. 5. The plug now has created a closed space which facilitates complete filling of the canal with acrylic cement, and also prevents the extension of the cement distal down the canal where it is not desired. By creating a closed space, this facilitates a rise in pressure in the cement during stem insertion which induces an optimum interface between cement and bone and also facilitates the penetration of cement into the interstices of the endosteal bone.

The invention described here is a simple means for creating a closed space in the medullary canal of long bones such as the femur, tibia, humerus and ulna in joint replacement surgery. While this invention has been described and exemplified in terms of its preferred embodiment, those skilled in the art can appreciate that modifications can be made without departing from the spirit and scope of this invention.

What is claimed is:

1. A device for plugging the medullary canal comprising the combination of:
   (a) a means for plugging the medullary canal made of a biologically compatible material, and wherein said plugging means has a proximal and a distal end and is round in cross-section and tapered from a larger diameter at the proximal end of the plug to a smaller diameter at the distal end of the plug, and wherein the proximal portion of the plugging means has tooth-like steps in which the diameter decreases in a series of steps, each perpendicular to the length of the plugging means and then tapering back out toward the distal end and approaching the original diameter, but with the outer diameter of each successive step being slightly less in diameter than the previous step as the steps progress from the proximal end toward the distal end of the plugging means, and wherein each step is a continuous ring about the plug, and;
   (b) a means for inserting the plugging means into the canal; and
   (c) a means associated with said plugging means and inserting means for engaging and disengaging the plugging means from the inserting means.

2. The combination defined in claim 1, wherein the inserting means is a long, narrow flexible shaft with a proximal end and a distal end capable of being easily inserted into the medullary canal, and wherein the shaft has incremental measurements marked on the shaft to indicate how deep the shaft has been inserted into the canal.

3. The device of claim 1, wherein said plugging means contains at least one or more longitudinal notches on the proximal portion of the plug.

4. The combination defined in claim 1, wherein the means for engaging and disengaging the plugging means from the inserting means is comprised of threads on the distal end of the shaft of said inserting means which engage and disengage a threaded hole in the proximal end of the plugging means.

5. A plug for the medullary canal, wherein said plug has a proximal and distal end which is tapered from a larger diameter at the proximal end of the plug to a smaller diameter at the distal end of the plug, and wherein the proximal portion of the plug has tooth-like steps in which the diameter decreases in a series of steps, each perpendicular to the length of the plug and then tapering back out toward the distal end and approaching the original diameter, but with the outer diameter of each successive step being slightly less in diameter than the previous step as the steps progress from the proximal end toward the distal end of the plug, and wherein each step is a continuous ring about the plug.

6. A plug as defined in claim 5, wherein said plug contains at least one or more longitudinal notches of the proximal portion of the plug.

7. A plug as defined in claims 5 or 6, wherein a threaded hole is provided in the proximal end of the plug.

8. A plug as defined in claim 5, wherein said plug is made of ultrahigh molecular weight polyethylene.

9. A plug as defined in claim 8, wherein said ultrahigh molecular weight polyethylene plug is radiopaque.

* * * * *